United States Patent [19]
Patel

[11] 4,195,055
[45] Mar. 25, 1980

[54] VAPOR-PHASE MOVING-BOUNDARY INDICATOR

[75] Inventor: Gordhanbhai N. Patel, Morris Plains, N.J.

[73] Assignee: Allied Chemical Corporation, Morristown, N.J.

[21] Appl. No.: 911,565

[22] Filed: Jun. 1, 1978

[51] Int. Cl.² .............................................. G01N 21/06
[52] U.S. Cl. .................................. 422/56; 23/230 R; 116/206; 422/58
[58] Field of Search ................. 23/230 R; 422/56, 57, 422/58; 116/114 AM, 114 V; 73/358

[56] References Cited

U.S. PATENT DOCUMENTS

| | | | |
|---|---|---|---|
| 2,560,537 | 7/1951 | Anderson . | |
| 3,118,774 | 1/1964 | Davidson et al. . | |
| 3,243,303 | 3/1966 | Johnson . | |
| 3,414,415 | 12/1968 | Broad, Jr. . | |
| 3,615,719 | 10/1971 | Michel et al. | 73/358 |
| 3,768,976 | 10/1973 | Hu et al. | 116/114 V |
| 3,844,718 | 10/1974 | Cohen | 23/253 TP |
| 3,954,011 | 5/1976 | Manske | 116/114 V |
| 3,981,683 | 9/1976 | Larsson | 23/253 TP |
| 3,999,946 | 12/1976 | Patel et al. | 23/253 TP |
| 4,042,336 | 8/1977 | Larsson | 23/253 TP |

OTHER PUBLICATIONS

Wegner, Zeitschrift Fun Naturschung vol. 24b pp. 824-832 (1969).

*Primary Examiner*—R. E. Serwin
*Attorney, Agent, or Firm*—Robert J. North; Gerhard H. Fuchs

[57] ABSTRACT

A vapor-phase moving-boundary indicator, is described, which is useful for monitoring the time-temperature histories of perishable articles. The device functions by allowing a vapor to permeate through a porous substrate coated with an indicating solid which undergoes a color change upon contact with the vapor. As the vapor permeates through the substrate, a visible moving boundary is created between two colors and it advances as a function of time and temperature. This provides a visual record of the time-temperature exposure of the article.

13 Claims, 5 Drawing Figures

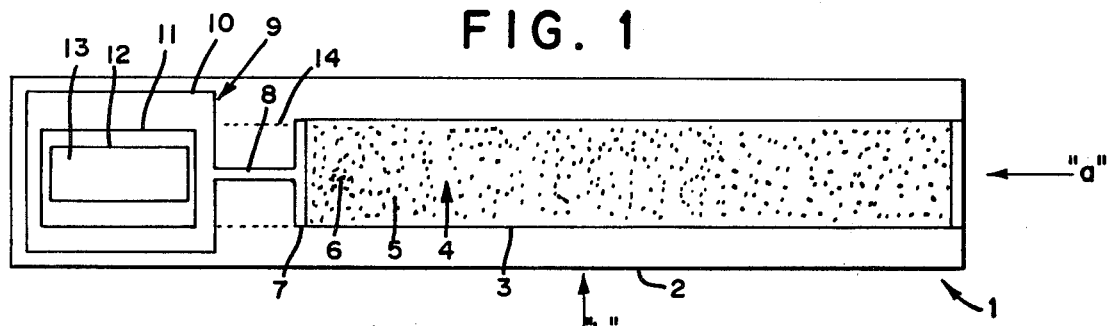
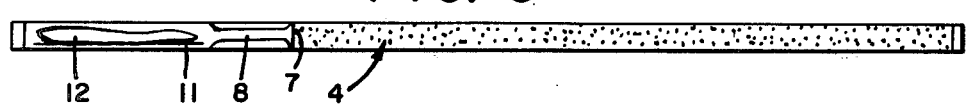
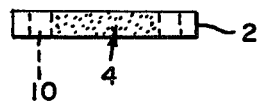
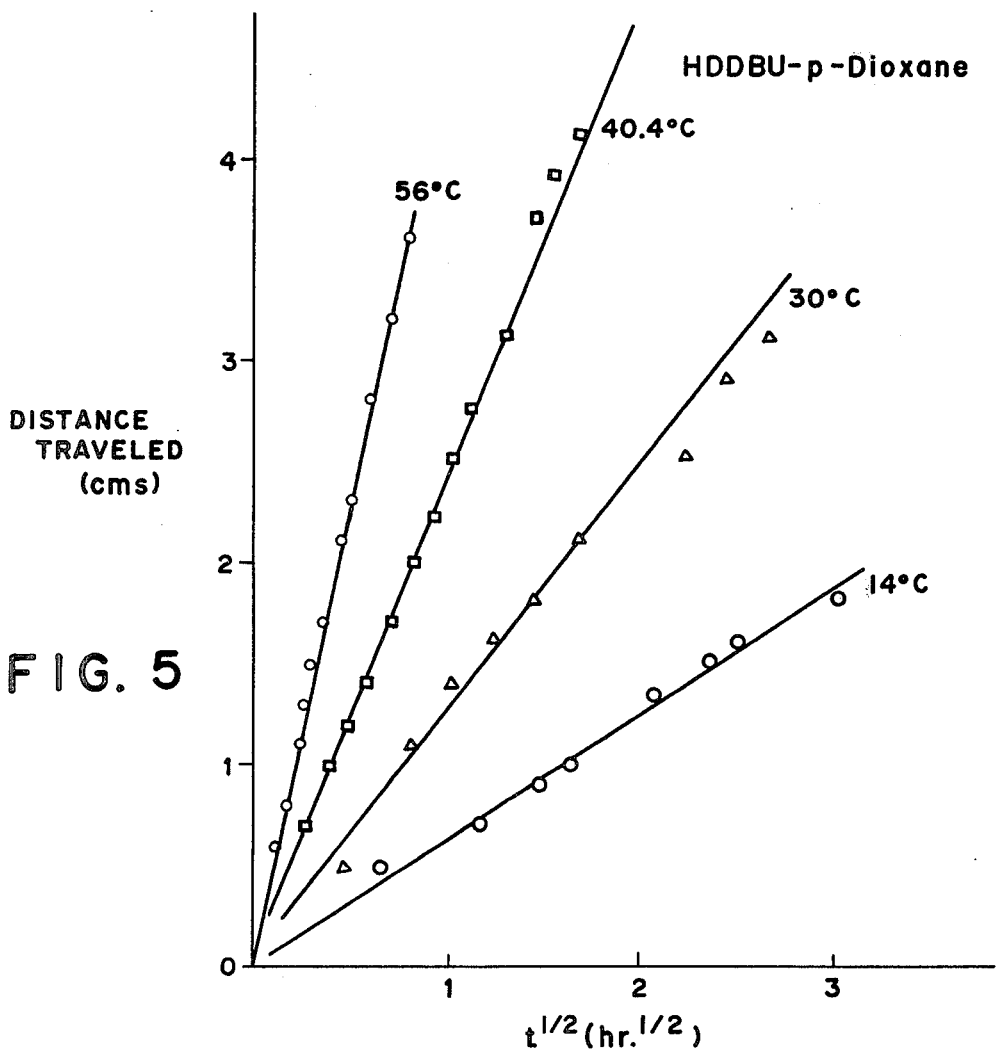

VAPOR-PHASE MOVING-BOUNDARY INDICATOR

BACKGROUND OF THE INVENTION

1. Field of the Invention

This invention relates to a device for monitoring the time-temperature history of an article in which a vapor is allowed to permeate through a porous substrate coated with an indicating solid, which undergoes a color change upon contact with the vapor, thus forming a moving boundary as vapor permeates through the substrate.

2. Brief Description of the Prior Art

A host of perishable products such as frozen foods, blood, vaccines and the like require a means for monitoring time-temperature shelf-life histories. Various indicators have been described in the prior art as meeting this need with varying success.

Indicators are known that use a liquid or liquid vapor for activating a color response when a predetermined shelf life has expired. For example, U.S. Pat. No. 3,844,718 discloses a defrost indicator which is activated by the contact of water or water vapor with a water-soluble ink supported on a hygroscopic substrate.

U.S. Pat. No. 3,768,976 discloses a time-temperature indicator that depends upon the rate of permeation of oxygen through a polymer envelope containing an aqueous solution of a red redox dye. Upon oxidation, the red dye turns colorless, indicating that the perishable has been exposed to too high a temperature for too long a time.

U.S. Pat. No. 3,915,719 discloses a temperature indicator in which a frozen liquid is separated from an indicating layer by a liquid-soluble barrier. When the frozen liquid thaws, a time delay is introduced by the rate of dissolution of the liquid soluble barrier. Only upon dissolution of this barrier does color indication occur.

There is a continuing need for improved indicators for monitoring the time-temperature histories of perishable products. Known successful devices require either liquids or gases. However, a device requiring vapor for initiation of the color response would be relatively less expensive to produce since less liquid would be required than in a device requiring liquid activation. Also, such a device would be without the disadvantage of depending upon the diffusion of an external gaseous reactant such as oxygen. Such as dependence can result in unwanted variations in device response for different environments. Moreover, the prior art does not suggest such that a device could be effectively used, in which device operation is based solely on the interaction between a vapor and an indicating solid capable of undergoing a color change, upon contact with the vapor.

SUMMARY OF THE INVENTION

We have unexpectedly found that such a device is very effective for monitoring the time-temperature history of an article wherein the device contains an indicator (comprising a porous substrate and deposited indicator composition) positioned in a chamber such that the outer surface of the indicator is in sealing contact with a portion of the internal surface of the chamber, such that vapor must permeate through the indicator to contact the indicating solid deposited thereon, thus forming a visual colored moving boundary as the vapor permeates throughout the substrate.

In accordance with this invention, there is provided a device for monitoring the time-temperature history of an article comprising:

(a) a closed vapor-impermeable container;

(b) a chamber forming one portion of solid container;

(c) an indicator, comprised of an adsorptive substrate, through which vapor can permeate at measurable rate, having a solid deposited on at least the outer surface thereof, said solid capable of undergoing a color response upon contact with vapor specified below, and said indicator positioned inside said container such that the outer surface of said indicator, containing said solid, is in sealing contact with a portion of the inner surface of the container;

(d) a source of vapor within said chamber, said vapor being capable of traveling through the substrate by permeation thereof, and being constrained by said sealing contact to travel through said substrate in order to contact said solid; and (e) means for providing said vapor at a given moment to the chamber; whereby a moving colored boundary is produced during travel of the adsorbed vapor throughout the indicator.

Further provided, is a process for monitoring the time-temperature history of an article comprising applying to the article the device of claim 1 and providing vapor to the chamber at the beginning of the monitoring.

Also provided is an article having the device of claim 1 applied thereto.

In addition, there is provided a process for making the device of claim 1 comprising the step of enclosing in a vapor-impermeable container:

(a) an indicator, comprised of an adsorptive substrate, through which a vapor can permeate at measurable rate, having a solid deposited on at least the outer surface thereof, said solid capable of undergoing a color response upon contact with vapor specified below, and said indicator positioned inside said container such that the outer surface of said indicator, containing said solid, is in sealing contact with a portion of the inner surface of the container;

(b) a source of vapor within said chamber, said vapor being capable of traveling through the substrate by permeation thereof, and being constrained by said sealing contact to travel through said substrate in order to contact said solid; and (c) means for providing said vapor at a given moment to the chamber.

BRIEF DESCRIPTION OF THE FIGURES

FIG. 1 is an illustration of the top view of one modification of the basic invention device showing the indicator 4 positioned inside of chamber 3.

FIG. 2 is an end view of the above device from position "a", designated in FIG. 1.

FIG. 3 is a side view of the above device from the position, "b", as designated in FIG. 1.

FIG. 5 is a plot of distance travelled vs. $t^{\frac{1}{2}}$ for the p-dioxane/partially polymerized HDDBU system of Example 2 at different temperatures.

DESCRIPTION OF THE INVENTION AND PREFERRED EMBODIMENTS

Figure 4:
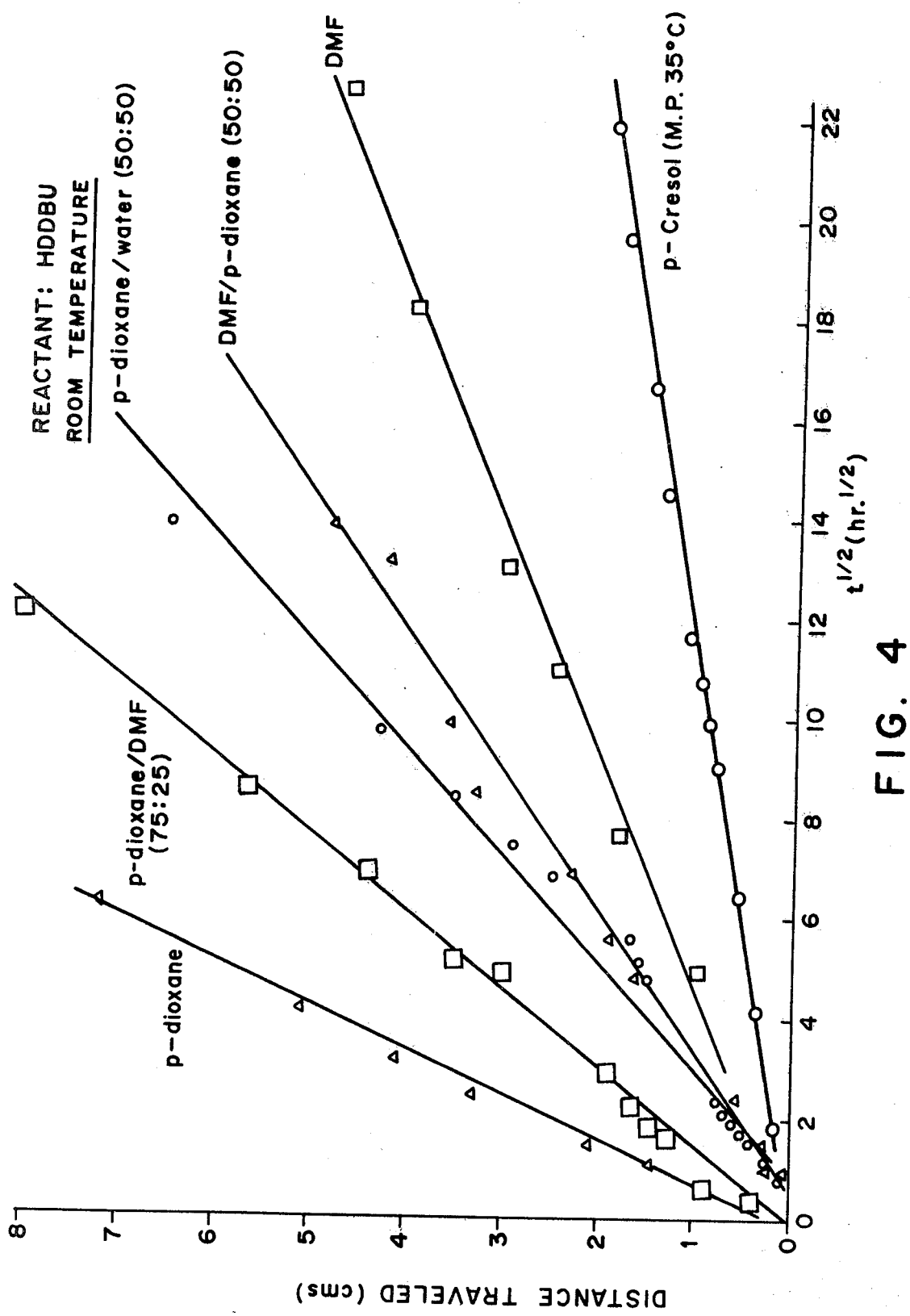
FIG. 4 is a composite plot of distance travelled by the moving boundary vs. $t^{\frac{1}{2}}$, the square root of the time required to travel that distance for the devices of Examples 1, 3 and 8.

The invention device basically comprises the elements of a container, a chamber which is positioned inside the container, an indicator situated inside the chamber and a vapor source. The novel feature of the device is that the indicator is positioned inside the chamber in sealing contact with a portion of the inner surface of the chamber such that vapor is constrained to permeate through the indicator to contact indicating solid on the surface of the indicator thereby producing a color response. As the vapor permeates longitudinally through the length of the indicator, the color response takes the form of a moving boundary comprised of vapor-contacted indicating solid and non-contacted indicating solid.

A description of a preferred embodiment of the invention device can be readily made by reference to FIG. 1, FIG. 2 and FIG. 3 which illustrates a preferred embodiment of the invention device. The device 1 comprises a vapor-impermeable container 2, in which is housed indicator 4, comprised of an adsorptive substrate 5, on which is deposited indicating solid 6, said indicator housed in indicator chamber 3, positioned in such a manner that said indicator is flush against the inner surface of the chamber 3 forming sealing contact 7. Vapor-entry chamber 8 connects indicator chamber 3 with vapor source 9 which comprises vapor chamber 10, evaporation substrate 11, solvent reservoir 12 and solvent 13.

Device operation comprises initially rupturing frangible solvent reservoir 12, as for example, by hand pressure to release solvent into the system. This action is designated as the starting point of the monitoring process. As solvent 13 is released from reservoir 12, it contacts evaporation substrate 11 and is absorbed. Evaporation of solvent from the substrate forms vapor which can activate the indicator 4. Formed vapor travels through vapor chamber 10, through vapor-entry chamber 8 and arrives at the indicator at sealing point 7. Due to that fact that sealing point 7 prevents vapor from diffusing around the sides of indicator 4, it is constrained to permeate through adsorptive substrate 5. While said vapor permeates through substrate 5, it permeates to the surface of said substrate and contacts indicating solid 6, which then exhibits a color response, usually being a color change. As the vapor travels the length of indicator 5, a corresponding color response occurs on the surface of the indicator and thus the vapor-transport creates a colored moving boundary. The rate of travel of the moving boundary between two selected points on the surface of the indicator can be regulated by suitable choice of vapor, adsorptive substrate 5 and indicating solid 6, such that the time required for the boundary to travel between the points corresponds to a predetermined time-temperature history of an article at a particular temperature such as the shelf-life of the article.

Knowledge of the time required for the moving boundary to travel between two points on the surface of the indicator at a particular temperature, for a device of known geometry and vapor-indicator combination, allows the time of thermal annealing to be monitored at known temperature, or conversely, the temperature to be monitored during a known time interval.

The device of this invention can be used for monitoring the time-temperature histories of perishable products over a temperature range of about $-70°$ to $+150°$ C. and from times ranging from about 1 minute to one year, depending on the choice of vapor, indicator and barrier materials, which will be obvious to one skilled in the art from the disclosure herein. The device can be utilized in a variety of ways including attaching the device to the article to be monitored by means of an adhesive-type backing on the container or by placing the device in close proximity to the article in the area in which it is being stored, for instance on the inside of a cabinet door, or on a wall or shelf of the storage facility.

The function of the sealing contact is to create a characteristic rate of travel for the moving boundary and a characteristic activation energy for such travel rate, such that the time required for the moving boundary to travel between two predetermined points on the indicator can be predictably controlled as a function of temperature.

The sealing contact in the device must be positioned between the vapor and indicator such that the vapor is constrained to permeate through the indicator prior to contacting the indicating solid such that the color response does not occur simultaneously with release of vapor to the system. In addition, the adsorptive substrate must be measurably permeable to said vapor and must not be dissolved by said vapor during the monitoring period. However, a slight swelling effect of the adsorptive substrate may occur during the monitoring, and may be tolerated provided that reproducible kinetics can be obtained for boundary movement.

By the term "sealing contact" is meant the state of the juncture between the outer longitudinally exposed surface of the indicator and the inner surface of the indicator chamber in which the indicator is positioned. The degree of contact between the outer surface of the indicator and the inner surface of the chamber must be such that vapor is not allowed to travel between the inner surface of the chamber and the outer surface of the indicator. This can be accomplished in a variety of ways such as choosing an indicator of such volume and geometry as to "snugly" fit the inside volume of the chamber to form the sealing contact. Alternately, the indicator can be glued or adhered to the inner surface of the chamber by a suitable adhesive, which must not be soluble or chemically reactive toward the vapor used in the device. It is preferred however, to shape the indicator chamber to the volume and geometry of the indicator, in that portion of the indicator chamber in which the indicator is to be positioned. This is usually accomplished by "sealing" the container material around the indicator to obtain a tight fit and maximum contact between indicator and chamber.

In referring to the rate of travel of the moving boundary, the term "moving boundary rate" is used herein. By the term "energy of activation of the system" is meant the value of $E_{act.}$, obtained by measuring the moving boundary rate during device operation at two or more temperatures. The time required for the boundary to move a certain distance, ln t as the ordinate, is plotted versus 1/T as the abscissa and the $E_{act.}$ energy of activation is calculated from the slope of the resulting straight line curves, by known methods in the art.

The moving boundary rate is characteristic for a particular device of a particular geometry and having a particular vapor-indicator combination. Thus, devices having identical geometries and vapor-indicator combinations will possess substantially identical moving boundary rates at identical temperatures.

the container of the device is a closed vapor-impermeable structure housing the vapor source, indicator chamber and indicator of the device. The container operates to contain and prevent any vapor from escaping out of the device and also to provide an observable view of the developing moving boundary during the monitoring period. Representative examples of suitable materials for constructing the container include polyethylene, polypropylene, polyester, such as polyethylene and polybutyelene terephthalate, and polyamide, such as nylon 66. A preferred material is polyester.

In addition, the container may also have an adhesive backing to allow a means for attaching the device to an article to be monitored.

A further embodiment includes a "masking portion" on the front (top) of the device containing a small "window" at one point of the indicator. Operation of the device is conducted wherein the device is calibrated such that a particular monitoring period at a predetermined temperature will cause the moving boundary to appear in the window, thus signalling a "go-no go" situation in which the monitoring period has expired.

The size and design of the container can be varied to suit the particular article to be monitored. A limitation on the size of the device is that it must be large enough to exhibit an observable color response under the conditions of monitoring.

The chamber of the device is a portion of the inside of the container which acts as a holder for the indicator and also in which the moving boundary can be observed. The chamber, also referred to as the "indicator chamber" is generally formed by shaping the chamber material to fit the longitudinally exposed surface of the indicator. The chamber can be of any vapor-impermeable material such as polyethylene, polypropylene, polyester, such as polyethylene and polybutylene terephthalate, and polyamide, such as nylon 66. It is preferred to use the container material in constructing the chamber.

The indicator chamber is connected to the vapor source by means of a vapor-entry chamber as illustrated in FIG. 1. This particular chamber can be constructed of materials used for the container and indicator chamber as described above. It is preferred to use the same material as that used for the indicator chamber. As illustrated in FIG. 1, chamber 8 is narrow, which acts to increase the time required for vapor to reach and contact the indicator. Alternately, a wider vapor-entry chamber can be utilized such as chamber 14 in FIG. 1, which is outlined by dotted lines.

The indicator of the device must be capable of exhibiting a visual color response upon contacting a vapor, permeating to the surface of the indicator to contact the indicating solid deposited thereon. Upon contact with said vapor, the indicator undergoes a color response, preferably a color change, on its exposed surface which position correspondingly moves as vapor travels through said indicator. The reason as to why the indicating solid, undergoes a color response upon contacting with said vapor is not clearly understood and may be due to a variety of mechanisms such as dissolution of a portion of the indicating solid by the vapor, a change in the crystallinity of the indicating solid, a change in the crystal structure of the indicating solid, formation of a vapor-solid complex, or the like. Regardless of the mechanism underlying the color response, the incorporation of a vapor-indicator combination into the device system is not specifically directed or predicated upon one particular mechanism, but is based generally upon the observed fact that an indicating solid is capable of undergoing a color response upon contact with a vapor and capable of forming a visual moving boundary.

The indicator comprises an indicating solid deposited on an adsorptive substrate. The substrate can be any solid vapor-permeable material which acts as a support for the solid and a means of transport for the vapor by adsorption during the monitoring process. Representative examples of the adsorptive support are filter paper, cotton and wool. Preferred material used as the adsorptive support is filter paper.

Size and volume of the adsorptive support will vary with the intended application and will be obvious to one skilled in the art.

Shape of said support can be flat, rectangular or cylindrical. Preferred is a flat shape since a larger observable exposed surface is possible.

The indicating solid can be deposited on the adsorptive substrate by means of contacting the substrate with a solution of the indicating solid and allowing the solvent to evaporate. Alternately, the indicating solid can be dispersed in a suitable binder medium known in the art such as shellac, varnish, acrylics, epoxies, glues or adhesives, and then applied to the substrate.

The indicating solid is deposited on the surface of the adsorptive substrate and as a result may also permeate into the internal matrix of the support. However, only the exposed surface of the indicator is available for use in monitoring time-temperature histories.

The indicating solid may be uniformly dispersed over the surface of the indicator or may be placed at various intervals along the length of the porous substrate which correspond to certain predetermined time periods at a given temperature. Thus, such a device can operate wherein a "visible moving boundary" is not created continuously during the monitoring period, but only appears as the "end-point" of the measuring period.

The indicating solid can be any solid material which undergoes a color response, i.e., a color change, upon contacting said vapor. This includes a host of compounds including dyes, pigments and other colored or white solids which undergo a color change, as a response, upon contacting a vapor.

Representative examples of dyes and pigments include ethyl violet, malachite green, and the like. Also included are those dyes and pigments listed in the reference "The Chemistry of Synthetic Dyes and Pigments" by H. A. Lubs, Copyright 1955, Reinhold Publishing Co., *ACS Monograph Series No.* 127, which is hereby incorporated by reference.

A preferred class of indicating solids are diacetylene compounds, or mixtures thereof, wherein said compound contains at least one conjugated diyne group, i.e., $-C\equiv C-C\equiv C-$ per molecule. Diacetylene compounds are known in the art, including methods of preparation, and are adequately described in U.S. Pat. No. 3,999,946 (Patel et al. to Allied Chemical, 1976) which is hereby incorporated by reference. The diacetylene compounds typically contain at least one substituent selected from the group consisting of alkyl, aryl, sulfonate, urethane and alcohol derivatives and preferably the diacetylene contains at least one urethane substituent, and more preferably two urethane substituents. In a particularly preferred embodiment, the substituents are identical. Representative examples include those of the formula:

RNHCO—O—(CH$_2$)$_n$—C≡C—C≡C—(CH$_2$)$_m$—O—CONHR' where n and m can be the same or different and are at least 1; and wherein R and R' can be the same or different and are alkyl, substituted aryl and unsubstituted derivatives. Preferred diacetylenes useful in the instant invention include:

5,7-dodecadiyn-1,12-diol bis(butoxycarbonylmethylurethane), 4DBCMU,
5,7-dodecadiyn-1,12-diol bis(n-hexylurethane), 4DnHU,
5,7-dodecadiyn-1,12-diol bis(n-butylurethane), 4DnBU,
2,4-hexadiyn-1,6-diol bis(butylurethane), HDDBU,
2,4-hexadiyn-1,6-diol bis(m-tolylurethane), HDDmTU,
2,4-hexadiyn-1,6-diol bis(o-methoxyphenylurethane), HDDoMPU,
2,4-hexadiyn-1,6-diol bis(p-chlorophenylurethane), HDDpCPU,
2,4-hexadiyn-1,6-diol bis(o-chlorophenylurethane), HDDoCPU and
4,6-decadiyn-1,10-diol, DDD.

The diacetylene compound, or mixture thereof, can also be partially polymerized, for example, by solid state polymerization induced by thermal annealing, or high energy radiation such as ultraviolet, alpha-, beta-, electron- or gamma-radiation.

Some partially polymerized diacetylenes thus produced are blue. For example, HDDnBU, partially polymerized by exposure of the solid monomer to ultraviolet radiation for about 0.5 to 10 minutes, is a blue solid, containing about one weight percent polyacetylene derived from the monomer. Partially polymerized diacetylenes are generally an intimate mixture of monomer and polyacetylene approaching a solid solution, where the polyacetylene is present in an amount of up to about 10% by weight of the mixture. Other partially polymerized diacetylenes useful in the invention are those derived from the diacetylene monomers listed above.

Some partially polymerized diacetylenes which are blue in color undergo a color response to a red color generally, when contacted with certain vapors. For example, partially polymerized HDDBU upon contacting with acetone vapor undergoes a color response to a red color.

Polymeric materials, containing from about 10% to 100% by weight of polyacetylene, such as fully polymerized diacetylene, which can also undergo a color response upon contact with a vapor are also included as indicating solids in the instant invention. An example of a fully polymerized diacetylene which can be used as indicating solid is poly[5,7-dodecadiyn-1,12-diol bis(butoxycarbonylmethylurethane)], poly 4DBCMU.

Mixtures of solids, wherein each solid exhibits a characteristic color response upon contact with vapor, but wherein the mixture exhibits a combined different overall color response when contacted with vapor, are also a subject of this invention. For example, a colorless diacetylene such as HDDmTU, which undergoes a color response to a blue color upon contact with a vapor can be combined in simple mixture with a yellow dye or pigment. The initial yellow mixture upon contact with vapor will undergo a change to green, the addition color of the two subtractive primaries, yellow and blue. In a similar manner, other color responses can be generated from mixtures of two or more differently colored solids, which will be obvious to one skilled in the art from this disclosure. Thus, the instant invention also includes a solid diacetylene compound and a solid selected from the group consisting of dyes, pigments, or mixtures thereof.

Some indicating solids have the property of being able to exhibit two color responses upon contact with certain vapors. For example, metallic-colored poly 4DBCMU when contacted with chloroform vapor, undergoes a color response from metallic color to red, and then shortly thereafter, a color response from red to yellow. Both color responses can be utilized in monitoring time-temperature histories of perishable products. The reason the second color response occurs is not clearly understood but may be due to a partial solubility of the colored material in the condensed vapor.

Further included among solids useful in the instant invention are those solids existing in an inactive form, not capable of undergoing a color response upon thermal annealing, but capable of undergoing conversion to an active form upon contacting with a vapor and said active from being capable of undergoing a color response upon thermal annealing. Novel inactive forms of such solids, and their methods of preparation, are described in U.S. application Ser. No. 938,174, which is hereby incorporated by reference. Representative examples of inactive form include HDDmTU, HDDoMPU, HDDpCPU and HDDoCPU, or mixtures thereof, described above, which can be converted to the active forms in the device by contacting with p-dioxane, dimethylformamide or pyridine vapor, or mixtures thereof.

Vapor in the present invention device is stored as a condensed liquid, and is positioned such that upon release, formed vapor is constrained to permeate through the adsorptive substrate before contacting the indicating solid. The vapor must be able to permeate through the substrate without significantly dissolving said substrate, and preferably the vapor in the condensed liquid state has a boiling point of at least about 25° C., or higher at atmospheric pressure.

Representative examples of vapor useful in the instant invention include $C_3$–$C_6$ linear or branched acyclic alkyl ketones; halogenated $C_1$–$C_3$ alkanes, containing 1–4 halogen atmos being fluorine, chlorine, bromine, iodine or mixtures thereof; $C_3$–$C_6$ N,N-dialkylalkanoamides, wherein said alkyl groups may be the same or different and may be linear or branched; $C_1$–$C_3$ monohydric alkyl alcohols; $C_1$–$C_4$ saturated alkanoic monocarboxylic acids, wherein said alkane portions may be either linear or branched; $C_2$–$C_6$ alkyl sulfoxides and $C_2$–$C_6$ alkyl ethers, wherein said alkyl groups may be the same or different and may be linear or branched; cyclic $C_4$–$C_9$ alkyl ethers, said alkyl groups being either linear or branched; $C_7$–$C_9$ alkylphenols, said alkyl groups being either linear or branched and said phenol being either mono-, di- or trisubstituted; $C_5$–$C_{10}$ heterocyclic nitrogen compounds, containing up to 2 ring nitrogen atoms, and 1 or 2 aromatic rings, being fused or separated; phenol, water, equivalents of the above-recited compounds or mixtures thereof. Preferred vapors for use in the invention device are acetone, methyl ethyl ketone, dichloromethane, chloroform, carbon tetrachloride, dimethylsulfoxide, dimethylformamide, dimethylacetamide, methanol, ethanol, isopropanol, acetic acid, water, p-dioxane, p-cresol, phenol, pyridine, equivalents or mixtures thereof.

Means for providing vapor to the container being the vapor source, at the beginning of the monitoring process is positioned inside the container and comprises a frangible solvent reservoir, containing solvent, and supported on an evaporation substrate, said means connected to the vapor-entry chamber, which is in turn connected to the indicating chamber. The reservoir being frangible, it is easily ruptured, as for example, by hand pressure at the beginning of the monitoring period. The solvent is allowed to vaporize from a wetted evaporation substrate, e.g., a porous substrate, such as filter paper, which facilitates evaporation. The solvent reservoir can be constructed of a variety of materials with the proviso that the reservoir material is not significantly soluble in the solvent, but may be slightly swelled during the monitoring process. In one embodiment, the material is sufficiently non-permeable to the solvent that escape of solvent to the container does not occur prior to the desired monitoring period. Representative materials that can serve as the solvent reservoir include thin walled glass, aluminum foil and frangible but vapor-impermeable plastic. A preferred material is glass.

A preferred device of the invention is wherein the indicator is comprised of: blue-colored partially polymerized 5,7-dodecadiyn-1,12-bis(butoxycarbonylmethylurethane), 4DBCMU, as indicating solid, deposited on filter paper as the adsorptive substrate, and wherein the vapor is chloroform, acetone p-dioxane, dimethylformamide or mixtures thereof.

Other preferred indicating solid/vapor device system combinations include HDDnBU/acetone and HDDmTU/dioxane.

The energy of activation of the device, $E_{act.}$, can be calculated by measuring the time required for the moving boundary to travel a certain specified distance during device operation at two or more temperatures. The energy of activation of the device is a measure of the temperature dependence of the rate of the advancement of the boundary. The time required to travel a certain distance, represented by $\ln t$ as the ordinate, is plotted versus $1/T$ as the abscissa and the energy of activation is calculated from the slope of the resulting straight line curves, by known methods in the art. In general, devices having higher energies of activation, will undergo color responses at relatively higher rates at higher temperatures, as compared with the rates at lower temperatures, than for devices having lower activation energies.

Also provided in the instant invention is a process for monitoring the time-temperature history of an article comprising applying to the article the device of this invention and providing vapor to contact the indicator at the beginning of the monitoring period. The device may also contain a means, by which it can be readily attached to an article to be monitored, preferably an adhesive backing. Means for providing vapor to the device are discussed hereinabove and can be a frangible solvent reservoir, as described herein, which can easily be activated by hand pressure, for example. The monitoring process can be controlled at a temperature of about $-70°$ to $+150°$ C.; at atmospheric pressures and even reduced pressures in a partial vacuum.

Also a part of the instant invention is an article having the device of the invention, as described herein, attached thereto.

A process for making the device of this invention is also included as a part of the instant invention and comprises enclosing in a vapor-impermeable container:

(a) an indicator, comprised of an adsorptive substrate, through which a vapor can permeate at a measurable rate, having a solid deposited on at least the outer surface thereof, said solid capable of undergoing a color response upon contact with vapor specified below, said indicator positioned inside said container such that the outer surface of said indicator, containing said solid, is in sealing contact with a portion of the inner surface of the container;

(b) a source of vapor within said chamber, said vapor being capable of traveling through the substrate by permeation thereof, and being constrained by said sealing contact to travel through said substrate in order to contact said solid; and (c) means for providing said vapor at a given moment to the chamber.

The nature of the container, chamber, indicator, indicating solid, substrate vapor and means for providing vapor to the device are fully and adequately described hereinabove. The device indicator can be prepared by contacting the adsorptive substrate with a solution of the indicating solid and allowing the solvent to evaporate. Alternately, the indicating solid may be dispersed in a medium such as a binder and applied to the substrate. The indicator can then be positioned inside the chamber, in sealing contact therewith, by means of a sealer, such as a hot press sealer, hot air sealer and pressure sensitive adhesives. Preferred is a hot press sealer. The other components of the device including the vapor source solvent reservoir and evaporative substrate, are also sealed in the container by means of the sealer to form the completed device.

The following examples are illustrative of the best mode of carrying out the invention, as contemplated by us, but should not be construed to be limitations on the scope or spirit of the instant invention. Parts are by weight where given unless otherwise indicated.

EXAMPLE 1

PREPARATION AND USE OF THE VAPOR PHASE MOVING BOUNDARY INDICATOR

1. Preparation of the Device

Three devices similar to that illustrated in FIG. 1 were prepared. The indicator in each device was prepared by spraying a 10 cm. × 10 cm. square of Whatman No. 1 filter paper with a solution of 1 gram HDDnBU monomer in 20 ml of acetone solvent. After spraying, the solvent was allowed to evaporate and the coated strip was subjected to ultraviolet radiation from a 15 watt ultraviolet lamp (General Electric Co.) to yield partially polymerized HDDnBU, as the indicating solid containing about one weight percent polymer. The square was then cut into 0.5 cm. × 10 cm. strips and each strip was then firmly encased and sealed on three sides in a 1 × 14 cm piece of 2 mil thick polyester. Next, a 0.5 × 2.0 cm piece of porous substrate saturated with acetone was placed into the other end of the chamber and the entire assembly sealed.

2. Description of the Runs

The beginning of the measurement, i.e., the development of the colored moving boundary, was taken when the entire system was sealed and vapor began to diffuse into the color indicating strip at room temperature. Upon contact with vapor the blue partially-polymerized HDDnBU on the surface of the strip, turned red and at that point, formed a visual red-blue boundary. As the vapor diffused through the indicating strip, the boundary moved correspondingly, thus forming a colored moving boundary history of the time-temperature exposure. The three devices separately contained different vapors, acetone, p-dioxane and dimethylformamide, and were tested to determine the dependence of the rate of advancement of the moving boundary upon the particular vapor used. Table 1 below lists times required for the moving boundary to travel a certain distance, the square root of the required time, and the distance travelled in centimeters for each of the device systems.

TABLE I

| Acetone | | | p-Dioxane | | | Dimethylformamide | | |
|---|---|---|---|---|---|---|---|---|
| Time (hrs.) | $t^{\frac{1}{2}}$ | Distance travelled in cms. | Time (hrs.) | $t^{\frac{1}{2}}$ | Distance travelled in cms. | Time (hrs.) | $t^{\frac{1}{2}}$ | Distance travelled in cms. |
| 0.66 | 0.81 | 1.3 | 1.16 | 1.08 | 1.5 | 1 | 4.9 | 1.0 |
| 1.25 | 1.12 | 2.5 | 2.33 | 1.53 | 2.3 | 2 | 7.6 | 1.8 |
| 1.66 | 1.29 | 3.5 | 3.33 | 1.83 | 2.7 | 5 | 10.9 | 2.5 |
| 2.08 | 1.44 | 4.2 | 6.00 | 2.45 | 3.3 | 7 | 13.0 | 3.0 |
| 2.33 | 1.53 | 5.0 | 10.00 | 3.16 | 4.1 | 14 | 18.3 | 4.0 |
| 3.83 | 1.95 | 6.0 | 17.33 | 4.16 | 5.1 | 21 | 22.5 | 4.7 |
| 5.16 | 2.27 | 7.5 | 28.50 | 5.34 | 6.1 | 28 | 25.9 | 5.0 |
| 8.00 | 2.83 | 9.5 | 40.00 | 6.30 | 7.2 | 35 | 29.0 | 5.1–5.3 |
| | | | 42.83 | 6.54 | 7.9 | | | |
| | | | 48.00 | 6.93 | 8.9 | | | |

FIG. 4 includes plots of the distances travelled by the moving boundary versus the square root of the times required for travel of that particular distance for the devices utilizing p-dioxane and dimethylformamide of Example 1. The plot of the device employing acetone is not displayed since the curve on this scale is almost identical to that for p-dioxane, but has slightly higher slope. The plots illustrate linear relationships which indicate that the process of developing the moving boundary is diffusion controlled.

EXAMPLE 2

EFFECT OF TEMPERATURE ON THE RATE OF TRAVEL OF THE MOVING BOUNDARY

Four runs were conducted utilizing the device described in Example 1, in which p-dioxane was the vapor and blue-colored partially polymerized HDDnBU was the indicating solid. The runs were conducted at different temperatures ranging from 15° to 56° C. The results of the runs, plotted as distance travelled (in centimeters vs. $t^{\frac{1}{2}}$ for each particular temperature), are illustrated in FIG. 5.

As is seen from FIG. 5, there is a linear relationship between the distance travelled and the square root of the time required for that particular distance travelled over this temperature range, indicating that the process is diffusion controlled. Also illustrated is the fact that the slope of the curve is greater at higher temperatures, such that the moving boundary develops and advances at a faster rate at higher temperatures.

The activation energy, $E_{act.}$, was calculated for the p-dioxane/partially polymerized HDDnBU system by plotting the natural logarithm of the time required for the moving boundary to travel a certain distance, here, 2, cm., versus 1/T, where T is the absolute temperature of the measurement. The activation energy for the p-dioxane system was found to be 19.5 kcal/mol. A similar measurement for the same system but using chloroform as the vapor yielded a value of 30.3 kcal/mol.

EXAMPLE 3

USE OF A SOLID HAVING A HIGH VAPOR PRESSURE AS A SOURCE OF VAPOR

The devices used in this example were similar to those described in Example 1, except that instead of employing liquid solvents as the source of vapor, organic solids having a high vapor pressure at room temperature were used, i.e., phenol and p-cresol. The indicating solid used was partially polymerized HDDnBU as indicated in Example 1. The measurements were conducted at room temperature and the results are tabulated below in Table 2.

TABLE 2

| | Distance Travelled (cms.) | |
|---|---|---|
| Time (hrs.) | Phenol | p-Cresol |
| 0 | — | — |
| 2.5 | 0.1 | 0.1 |
| 3.6 | 0.2 | 0.1 |
| 16.8 | 0.5 | 0.4 |
| 24.3 | 0.6 | 0.4 |
| 40.8 | 0.8 | 0.6 |
| 49.5 | 0.9 | 0.7 |
| 72 | 1.1 | 0.8 |
| 97 | 1.2 | 0.9 |
| 115 | 1.4 | 1.0 |
| 136 | 1.5 | 1.1 |
| 211 | 1.7 | 1.3 |
| 281 | 2.2 | 1.5 |
| 331 | 2.3 | 1.6 |
| 384 | 2.4 | 1.8 |
| 480 | 2.7 | 1.9 |
| 672 | 2.9 | 2.1 |
| 792 | 3.0 | 2.2 |
| 1296 | 3.8 | 2.6 |
| 1704 | 4.2 | 2.8 |
| 2736 | 5.0 | 3.1 |

FIG. 4 illustrates a plot of the distance travelled by the moving boundary versus the square root of the time required for travel for the above described p-cresol containing device. The corresponding plot for the phenol device is not illustrated since on the same scale, it appeared substantially identical.

EXAMPLE 4

DOUBLE MOVING BOUNDARY INDICATOR

The device used in this example was similar to that of Example 1 except that chloroform was used as the vapor and partially polymerized 4DBCMU was the indicating solid. Contact of the chloroform vapor with the diacetylene polymer produced a moving red-blue boundary. Trailing the moving red-blue boundary, initially formed, was a moving yellow-red boundary, which was ascribed as being due to solubility of the extracted red polymer in the condensed vapor. The device operation was conducted at room temperature and the distance travelled by both boundaries for particular times are listed below in Table 3.

TABLE 3

| Time (min.) | $t^{\frac{1}{2}}$ (hr.) | Distance travelled (cm.) | |
|---|---|---|---|
| | | Blue-red | Red-yellow |
| 1 | 0.016 | 0.6 | — |
| 2 | 0.158 | — | 0.1 |
| 5 | 0.289 | 1.3 | 0.5 |
| 21 | 0.591 | 1.6 | 0.5 |
| 32 | 0.730 | 1.7 | 0.5 |
| 41 | 0.827 | 1.7 | 0.6 |

The plot of distance travelled by each boundary versus the square root of the required time illustrated that each boundary advanced along the indicating substrate at different rates, the blue-red boundary moving and developing faster than the trailing yellow-red one.

EXAMPLE 5

DEVICE USING INACTIVE DIACETYLENE INDICATING SOLIDS

The device used in this example was similar to that of Example 1 except that the source of vapor was in a frangible capillary containing solvent, an inactive form of HDDmTU monomer was used as the indicating solid, and the device was enclosed in a polyester container. Inactive HDDmTU monomer is inactive towards color changes upon exposure to thermal annealing, but is capable of being converted to an active form upon contacting with an organic vapor. The active form readily polymerizes to a blue color. Here, p-dioxane was used as the source of vapor for the conversion and the device operation was conducted at room temperature. The results are listed below in Table 4.

TABLE 4

| Time (hrs.) | log t | Distance travelled (cms.) |
|---|---|---|
| 0 | — | — |
| 2 | 0.301 | 1.8 |
| 3.25 | 0.512 | 2.6 |
| 4.50 | 0.653 | 3.0 |
| 5.75 | 0.760 | 3.9 |
| 7.50 | 0.875 | 4.3 |
| 9.75 | 0.989 | 4.7 |
| 13.75 | 1.138 | 5.7 |
| 24.00 | 1.380 | 7.4 |
| 26.75 | 1.427 | 7.8 |
| 28.00 | 1.447 | 8.5 |
| 32.00 | 1.502 | 9.2 |

As is seen from Table 4, no visible boundary occurred during the first two hours of device operation. Here, the vapor front moved ahead of the resulting developing moving boundary.

A plot of distance travelled vs. $t^{\frac{1}{2}}$ produced a straight line plot illustrating that the process is diffusion controlled.

EXAMPLE 6

USE OF SEMI-PERMEABLE MEMBRANE TO INTRODUCE OPTIONAL TIME DELAY INTO MOVING BOUNDARY

A device similar to that of Example 1 was used except that chloroform was the vapor, and a solvent reservoir was used, constructed of polyethylene, a semi-permeable polymer barrier, to introduce a time delay into the development of the moving boundary. This enables the monitoring capability of the device to be significantly enlarged. Partially polymerized 4DBCMU was used as the indicating solid, deposited upon Whatman filter paper No. 1 as the substrate. Device operation was conducted at room temperature and compared against another device as a control, being identical except for the polyethylene reservoir. The results are tabulated below in Table 5.

TABLE 5

| | Device with Solvent Barrier Distance travelled (mm) | | | Control Distance travelled (mm) | |
|---|---|---|---|---|---|
| $t^{\frac{1}{2}}$ (hrs) | blue-red | red-yellow | $t^{\frac{1}{2}}$ (hrs) | blue-red | red-yellow |
| 0.43 | 1.0 | — | — | — | — |
| 0.66 | 7.0 | — | 0.18 | 8 | — |
| 0.77 | 9.5 | — | 0.36 | 11 | 3 |
| 0.85 | 11.0 | — | 0.60 | 19 | 7 |
| 1.04 | 14.5 | — | 0.74 | 20 | 9 |
| 1.26 | 16.5 | 1.5 | 0.82 | 21 | 9 |
| 1.40 | 20.0 | 2.0 | 1.00 | 25 | 10 |
| 1.62 | 22.0 | 3.0 | 1.23 | 27 | 16 |
| 2.04 | 29.5 | 6.5 | 1.38 | 31 | 16 |
| 2.46 | 38.5 | 9.0 | 1.61 | 38 | 16 |
| | | | 2.06 | 51 | 17 |
| | | | 2.40 | 68 | 19 |

Plots of distance travelled vs. $t^{\frac{1}{2}}$ for the blue-red boundaries of both devices were linear showing a higher positive slope for the control vs the device with a solvent barrier.

EXAMPLE 7

USE OF AN ORGANIC DYE AS A COLOR INDICATOR

A device was constructed similar to that of Example 1 except that ethyl violet dye was the indicating solid and water was the vapor. Upon contact of the ethyl violet dye with water vapor, the dye dissolved forming a blue-violet color contrasted to its original green-gold color, thus forming a moving boundary as the water vapor moved along the indicator. Distance travelled by the boundary as a function of time is given in the following Table 6.

TABLE 6

| Time (hrs). | $t^{\frac{1}{2}}$ | Distance travelled (cm) |
|---|---|---|
| 3 | 1.73 | 1.1 |
| 19 | 4.41 | 2.0 |
| 23 | 4.79 | 2.1 |
| 42 | 6.52 | 3.3 |
| 70 | 8.41 | 3.7 |
| 119 | 10.91 | 4.8 |
| 185 | 13.60 | 5.6 |
| 209 | 14.49 | 6.1 |

A plot of distance travelled vs. $t^{\frac{1}{2}}$ showed a straight line, indicating that the process is diffusion controlled.

EXAMPLE 8

VAPOR PHASE MOVING BOUNDARY INDICATOR USING VAPOR MIXTURE

Four indicators were used which are identical to those of Example 1, except that one, (9A), contained 75:25% by volume of a p-dioxane/dimethylformamide solvent mixture; one, (9B), contained 50:50% by volume of a p-dioxane/dimethylformamide solvent mixture; another, (9C), a duplicate of (9B) contained 50:50% by volume of a p-dioxane/dimethylformamide solvent mixture; and the last, (9D), contained a 50:50% by volume mixture of p-dioxane/water. The indicating solid used was partially polymerized 4DBCMU and the devices were operated at room temperature. The distances travelled by the moving boundaries versus time are listed below in Table 7 for each indicator.

TABLE 7

| Device: | 9A | | | 9B | | | 9C | | | 9D | | |
|---|---|---|---|---|---|---|---|---|---|---|---|---|
| t(hrs.) | $t^{\frac{1}{2}}$ | distance (cm) | t(hrs.) | $t^{\frac{1}{2}}$ | distance (cms.) | t(hrs.) | $t^{\frac{1}{2}}$ | distance (cms) | t(hrs.) | $t^{\frac{1}{2}}$ | distance (cms) |
| 0.12 | 0.34 | 0.40 | 0.25 | 0.5 | 0.25 | 0.55 | 0.82 | 0.15 | 0.67 | 0.82 | 0.15 |
| 0.38 | 0.62 | 0.80 | 0.63 | 0.79 | 0.40 | 1.40 | 1.18 | 0.25 | 1.52 | 1.23 | 0.25 |
| 0.76 | 0.87 | 0.80 | 2.50 | 1.58 | 0.75 | 2.25 | 1.50 | 0.30 | 2.36 | 1.54 | 0.40 |
| 2.63 | 1.62 | 1.30 | 3.42 | 1.85 | 0.95 | 2.80 | 1.62 | 0.35 | 2.92 | 1.71 | 0.45 |
| 3.55 | 1.88 | 1.45 | 4.98 | 2.23 | 1.15 | 3.68 | 1.92 | 0.40 | 3.80 | 1.95 | 0.55 |
| 5.12 | 2.26 | 1.65 | 6.13 | 2.47 | 1.30 | 4.55 | 2.13 | 0.55 | 4.66 | 2.16 | 0.60 |
| 6.27 | 2.50 | 1.65 | 8.42 | 2.90 | 1.40 | 5.80 | 2.41 | 0.60 | 5.92 | 2.43 | 0.75 |
| 8.55 | 2.92 | 1.90 | 24.15 | 4.91 | 2.10 | 7.80 | 2.79 | 0.75 | 7.92 | 2.81 | 0.75 |
| 24.28 | 4.93 | 3.00 | 26.40 | 5.14 | 2.20 | 22.55 | 4.75 | 1.65 | 22.66 | 4.76 | 1.50 |
| 26.53 | 5.15 | 3.50 | 31.86 | 5.64 | 2.30 | 23.37 | 4.83 | 1.70 | 23.48 | 4.84 | 1.55 |
| 32.00 | 5.66 | 3.50 | 48.28 | 6.95 | 2.80 | 24.55 | 4.95 | 1.80 | 24.66 | 4.96 | 1.55 |
| 48.41 | 6.96 | 4.90 | 72.28 | 8.50 | 3.30 | 25.43 | 5.04 | 1.80 | 25.55 | 5.05 | 1.60 |
| 72.41 | 8.51 | 5.65 | 168.88 | 12.99 | 5.10 | 26.28 | 5.13 | 1.85 | 26.40 | 5.14 | 1.60 |
| 148.08 | 12.17 | 8.00 | | | | 27.75 | 5.27 | 1.85 | 27.17 | 5.28 | 1.65 |
| | | | | | | 28.95 | 5.38 | 1.85 | 29.07 | 5.39 | 1.65 |
| | | | | | | 31.23 | 5.59 | 1.90 | 31.35 | 5.60 | 1.70 |
| | | | | | | 46.98 | 6.85 | 2.30 | 47.06 | 6.86 | 2.50 |
| | | | | | | 54.48 | 7.38 | 2.60 | 54.60 | 7.39 | 2.90 |
| | | | | | | 71.13 | 8.43 | 3.30 | 71.25 | 8.44 | 3.50 |
| | | | | | | 95.13 | 9.75 | 3.60 | 95.25 | 9.76 | 4.30 |
| | | | | | | 170.80 | 13.07 | 4.40 | 191.82 | 13.85 | 6.50 |
| | | | | | | 191.70 | 13.84 | 4.80 | | | |

I claim:

1. In a device for monitoring the time-temperature history of an article comprising
   (a) a closed vapor-impermeable container;
   (b) a chamber forming one portion of said container;
   (c) an indicator, comprised of an adsorptive substrate, through which vapor can permeate at measurable rate, having a solid deposited on at least the outer surface thereof, said solid capable of undergoing a color response upon contact with vapor specified below, and said indicator positioned inside said container such that the outer surface of said indicator, containing said solid, is in sealing contact with a portion of the inner surface of the container;
   (d) a source of vapor within said chamber, said vapor being capable of traveling through the substrate by permeation thereof, and being constrained by said sealing contact to travel through said substrate in order to contact said solid; and
   (e) means for providing said vapor at a given moment to the chamber; whereby a moving colored boundary is produced during travel of the adsorbed vapor throughout the indicator; the improvement which comprises a diacetylene compound, or mixture thereof, containing at least one —C≡C—C≡C— group per molecule, as said solid.

2. The device of claim 1 wherein the container is constructed of a vapor-impermeable polymer.

3. The device of claim 2 wherein said vapor in the condensed liquid state has a boiling point of at least about 25° C. at atmospheric pressure.

4. The device of claim 2 wherein said vapor is a $C_3$-$C_6$ alkyl ketone, halogenated $C_1$-$C_4$ alkane containing 1 to 4 halogens, $C_3$-$C_6$ N,N-dialkylalkanoamide, $C_1$-$C_3$ monohydric alkyl alcohol, $C_1$-$C_4$ saturated alkanoic monocarboxylic acid, or lower alkyl ester thereof, $C_1$-$C_4$ nitroalkane, $C_2$-$C_6$ alkyl sulfoxide, $C_2$-$C_6$ alkyl ether, cyclic $C_4$-$C_6$ alkyl ether, $C_7$-$C_9$ alkyl phenol, $C_5$-$C_{10}$ heterocyclic nitrogen compound, phenol, water, equivalents or mixtures thereof.

5. The device of claim 4 wherein said vapor is selected from the group consisting of acetone, methyl ethyl ketone, dichloromethane, chloroform, carbon tetrachloride, dimethylsulfoxide, N,N-dimethylformamide, N,N-dimethylacetamide, methanol, ethanol, isopropanol, acetic acid, water, ethyl acetate, nitromethane, dimethyl sulfoxide, p-dioxane, p-cresol, phenol, pyridine, equivalents or mixtures thereof.

6. The device of claim 1 wherein said diacetylene compound is a diurethane.

7. The device of claim 6 wherein the diacetylene compound is selected from the group consisting of 5,7-dodecadiyn-1, 12-diol bis (butoxycarbonylmethylurethane), 5,7-didecadiyn-1,12-diol bis(n-hexylurethane), and 5,7-dodecadiyn-1,12-diol bis(n-butylurethane).

8. The device of claim 1 wherein said diacetylene compound, or mixture thereof, is partially polymerized and is a mixture containing up to about 10 weight percent polyacetylene.

9. The device of claim 1 wherein said solid further comprises a compound selected from the group consisting of dyes, pigments or mixtures thereof.

10. The device of claim 1 wherein said solid is in an inactive form, not capable of undergoing a color response upon thermal annealing, but capable of undergoing conversion to an active form upon contacting a vapor.

11. The device of claim 10 wherein said solid is 2,4-hexadiyn-1,6-diol bis(m-tolylurethane), 2,4-hexadiyn-1,6-diol bis(o-methoxyphenylurethane), 2,4-hexadiyn-1,6-diol bis(p-chlorophenylurethane), 2,4-hexadiyn-1,6-diol bis(o-chlorophenylurethane), or mixtures thereof, and said vapor is p-dioxane, dimethylformamide, pyridine, or mixtures thereof.

12. A process for monitoring the time-temperature history of an article comprising applying to the article, the device of claim 1 and providing vapor to the indicator at the beginning of the monitoring.

13. A process for making the device of claim 1 comprising the step of enclosing in a vapor-impermeable container:
(a) an indicator, comprised of an adsorptive substrate, through which a vapor can permeate at measurable rate, having a solid deposited on at least the outer surface thereof, said solid capable of undergoing a color response upon contact with vapor specified below, and said indicator positioned inside said container such that the outer surface of said indicator, containing said solid, is in sealing contact with a portion of the inner surface of the container;
(b) a source of vapor within said chamber, said vapor being capable of traveling through the substrate by permeation thereof, and being constrained by said sealing contact to travel through said substrate in order to contact said solid; and
(c) means for providing said vapor at a given moment to the chamber.

* * * * *